United States Patent [19]

Rebsdat et al.

[11] 4,186,106

[45] Jan. 29, 1980

[54] PROCESS FOR IMPROVING THE ACTIVITY OF USED SUPPORTED SILVER CATALYSTS

[75] Inventors: Siegfried Rebsdat, Burg; Sigmund Mayer, Burgkirchen; Josef Alfranseder, Marktl; Josef Riedl, Burgkirchen, all of Fed. Rep. of Germany

[73] Assignee: Hoechst Aktiengesellschaft, Fed. Rep. of Germany

[21] Appl. No.: 939,329

[22] Filed: Sep. 5, 1978

[30] Foreign Application Priority Data

Sep. 8, 1977 [DE] Fed. Rep. of Germany ....... 2740480

[51] Int. Cl.² .................. B01J 23/96; B01J 23/50; C07D 301/10; C07D 303/04
[52] U.S. Cl. .................................. 252/414; 252/412; 252/420; 260/348.34
[58] Field of Search ............... 252/414, 412, 420, 476; 260/348.34

[56] References Cited

U.S. PATENT DOCUMENTS

| 2,437,930 | 3/1948 | Bergsteinsson et al. | 260/348.34 |
| 2,764,598 | 9/1956 | Egbert | 260/348.34 |
| 4,033,903 | 7/1977 | Maxwell | 252/476 |
| 4,051,068 | 9/1977 | Rebsdat et al. | 252/414 |
| 4,094,889 | 6/1978 | Hayden et al. | 260/348.34 |
| 4,123,385 | 10/1978 | Rebsdat et al. | 252/414 |
| 4,125,480 | 11/1978 | Maxwell | 252/412 |

Primary Examiner—P. E. Konopka
Attorney, Agent, or Firm—Connolly and Hutz

[57] ABSTRACT

The activity of supported silver catalysts, which have been used for the direct oxidation of ethylene to ethylene oxide with molecular oxygen or air and to which from 1 to 1,000 parts, per 1 million parts of catalyst, of cesium and/or rubidium have been applied, is improved by washing the catalyst with an inert liquid prior to the application of cesium and/or rubidium.

12 Claims, No Drawings

PROCESS FOR IMPROVING THE ACTIVITY OF USED SUPPORTED SILVER CATALYSTS

Silver catalysts, the manufacture of which has been known for a long time and is described in various patent specifications, are employed for the manufacture of ethylene oxide by the oxidation of ethylene with oxygen or air. A substantial number of large-scale industrial installations for the manufacture of ethylene oxide operate in accordance with the silver catalyst process. In this procedure, usually only a fraction of the ethylene employed is reacted. The predominant proportion of the ethylene reacted is converted, with oxygen, into ethylene oxide on the support material impregnated with silver and the remainder is virtually completely converted into carbon dioxide and water.

In the course of time, the most diverse silver catalysts have been developed, and in particular with the aim of increasing the selectivity with respect to the preferred formation of ethylene oxide and of supporting the formation of $CO_2$ and water.

With rising prices of raw materials and increasing scarcity of raw materials, an increased selectivity of the catalysts is of particular economic importance. Thus, in recent years silver catalysts, the selectivity of which for ethylene oxide is up to 75%, compared with earlier types with a selectivity of only 65 to 70%, have been developed.

These catalysts, such as are described, for example, in German Offenlegungsschrift No. 2,300,512, are obtained by applying to an inert support material, such as, for example, $Al_2O_3$, at the same time as the silver, 0.0004 to 0.0027 g equivalent of a potassium, rubidium or cesium compound per kg of catalyst from an aqueous solution.

On the other hand, it is also known that silver catalysts lose their selectivity in the course of time, and after being used for a number of years must be replaced by new catalyst. Apart from the costs of materials, the exchange of an "exhausted" catalyst for a new one in large-scale industrial installations is extremely time-consuming and labor-intensive; in addition, it causes loss in production and high costs. Accordingly, there is the problem of whether it is possible to improve the selectivity of exhausted catalysts again by a simple treatment in order to avoid or put off for as long as possible the exchange for a new catalyst.

Such a process is described in German Pat. No. 2,519,599 according to which a supported silver catalyst, which has been in use in the direct oxidation of ethylene to ethylene oxide with molecular oxygen or air is impregnated with a cesium and/or rubidium nitrate solution in a water-containing aliphatic alcohol. In this process 1 to 1,000 parts by weight of cesium and/or rubidium or of a mixture thereof, is applied to one million parts by weight (mg/kg) of used catalyst. The catalyst treated in this manner has a considerably improved selectivity.

Surprisingly, it has now been found that the improvement of the selectivity of supported silver catalysts by application of 1 to 1,000 mg/kg of cesium and/or rubidium to the used catalyst can be further increased by subjecting the used catalyst to a washing process prior to the cesium and/or rubidium application.

It is, therefore, the object of the present invention to improve the activity of supported silver catalysts used in the direct oxydation of ethylene to ethylene oxide with molecular oxygen or air by subjecting the used catalysts, prior to the application of 1 to 1,000 parts of cesium, rubidium or a mixture thereof per one million parts of catalyst, to a wash with a liquid that is inert towards the catalyst.

Suitable washing liquids are inorganic as well as organic liquids or mixtures thereof. It is quite obvious, of course, that the liquids are inert towards the catalyst, that is to say that they do not poison it or damage it to a noticeable degree, for example as regards selectivity, activity and silver content.

As organic liquids there may be used, either individually or in admixture with one another, aliphatic, alicyclic or aromatic hydrocarbons; aliphatic, alicyclic or aromatic ethers, alcohols, and ketones; aliphatic or aromatic acids such as acetic acid, propionic acid, esters, amines, amides, or aldehydes such as acetaldehyde, or benzaldehyde. In general, sulfur-containing liquids will not be used since they act as a poison for silver catalysts.

It proved advantageous to use inorganic and/or organic liquids having a boiling point not exceeding 350° C., preferably not exceeding 250° C. and more preferably not exceeding 150° C. and not lower than 0° C., preferably not lower than 15° C. The washing liquid used thus has a boiling point in the range of from 0° to 350° C., preferably from 15° to 250° C., and more preferably from 20° to 150° C.

Preferred organic liquids to be used are aliphatic, alicyclic or aromatic hydrocarbons, preferably those having from 5 to 10 carbon atoms, for example pentane, hexane, heptane, petroleum ether (boiling range 40° to 70° C.), light gasoline (70° to 90° C.), cyclohexane, benzene, toluene, xylene; aliphatic, alicyclic or aromatic ethers, preferably aliphatic or alicyclic ethers having from 3 to 10 carbon atoms, for example diethyl ether, methylisopropyl ether, ethylene glycol methyl ether, ethylene glycol dimethyl ether, tetrahydrofurane, dioxane; aliphatic, alicyclic or aromatic ketones, preferably aliphatic ketones having from 3 to 10 carbon atoms, for example acetone, ethylpropyl ketone, methylethyl ketone, dipropyl ketone; aliphatic esters having from 3 to 10 carbon atoms, for example methyl acetate, ethyl acetate and butyl acetate; and aliphatic, alicyclic or aromatic alcohols, preferably aliphatic or alicyclic alcohols having from 1 to 6 carbon atoms, especially aliphatic alcohols having from 1 to 3 carbon atoms, for example methanol, ethanol, propanol and isopropanol, the said liquids being used either individually or in admixture with one another or with water.

Especially preferred organic liquids are aliphatic hydrocarbons having from 5 to 10 carbon atoms, petroleum ether, cyclohexane, benzene, aliphatic ethers having from 4 to 8 carbon atoms, dioxane, tetrahydrofurane, aliphatic ketones having from 3 to 6 carbon atoms, and aliphatic alcohols having from 1 to 3 carbon atoms, which are used either individually or in admixture with one another or with water.

In principle, pure water can also be used as washing liquid. When a mixture of water with an organic liquid is used, it proved appropriate to operate with a water content of the mixture of up to 50% at the most, preferably up to 20% by weight, calculated on the total liquid (mixture).

To wash the used catalyst different methods can be used. It is only necessary that the catalyst comes into contact with the washing liquid and is then freed from the major portion thereof.

It is also possible to repeat the treatment (washing) several times. The time for which the catalyst is in contact with the washing liquid is not critical, it may last from a few minutes to several hours or days. In general, it is in the range from 5 minutes to 5 days and preferably from 30 minutes to 48 hours, more preferably from 1 to 5 hours. The washing is performed by pouring the liquid over the catalyst in a container and then removing it by centrifugation, filtration, suction filtration or simply by decantation. The catalyst can be left to stand with the washing liquid for a longer or shorter period, optionally with stirring, whereupon the washing liquid is removed. To achieve the effect according to the invention it is generally sufficient to wash the catalyst once, but it may also be of advantage to repeat the washing procedure several times, preferably 1 to 5 times and more preferably 2 to 3 times. In the latter case it proved advantageous to use each time fresh washing liquid. Alternatively, the washing liquid can be poured over the catalyst in a fixed bed in one or several tubes, the washing liquid being introduced into the tubes at one end and discharged from the other. This procedure can likewise be repeated several times, preferably each time with a fresh washing liquid. When the washing liquid it poured over the catalyst, it may be advantageous to keep it for some time in the tube(s), preferably for 30 minutes to 49 hours, before it is drained. This type of washing is preferably carried out in industrial scale installations, where the catalyst is used as a fixed bed in the tubes of the reactor. In this case the reactor filled with the catalyst is charged with the washing liquid and the liquid flowing off is collected at the reactor outlet.

It is not necessary to wash the entire amount of used catalyst. The effect according to the invention can even be obtained by washing only a fraction of thereof, for example 30 to 70% by weight thereof.

The amount of washing liquid (for one or several washing procedures) depends on the amount of catalyst to be washed and, of course, is must be so large, that the catalyst comes into contact with the liquid. The amount of washing liquid (for a one time washing) is preferably at least one third, in parts by weight or volume, of the amount of catalyst in parts by volume. It proved advantageous to use approximately equal to five times and preferably two to three times the amount of washing liquid.

The temperature of the catalyst and the washing liquid during the washing procedure is not critical and depends, in the first place, on economical considerations. It is suitably below the evaporation temperature of the washing liquid and, generally, it is in the range of from 10° to 100° and preferably 20° to 50° C. Whether or not the washing is to be carried out under pressure also depends on practical consideration. In general, the catalyst is washed without the application of pressure. If, however, washing under pressure is desired, the pressure should be in the range of from 1 to 20 atmospheres gauge, preferably 1 to 5 atmospheres gauge.

After washing 1 to 1,000 mg/kg of cesium, rubidium or a mixture thereof (the proportion being not critical) is applied to the catalyst.

The second process step, i.e. the application of cesium and/or rubidium to the washed catalyst can be performed directly after the first step, i.e. the washing, or after drying of the catalyst to remove remainders of the liquid left behind after separation or flowing off of the catalyst.

For drying an inert gas may be passed through and/or the catalyst may be heated, optionally under reduced pressure to accelerate drying. The temperature used for drying is not critical, it depends on the washing liquid used and, if drying is performed at atmospheric pressure, it corresponds approximately to the boiling point of the washing liquid. Suitable drying temperatures are, for example in the range of about 20° to 250° C., preferably 50° to 150° C. Drying under reduced pressure is even possible at room temperature, i.e. at 15° to 25° C., or at 25° to 80° C., whereby the remainders of washing liquid adhering to the catalyst after separation of the major portion thereof are completely evaporated. Drying can also be accelerated by heating and simultaneously passing over an inert gas. Suitable inert gases are preferably non inflammable gases which do not promote combustion such as nitrogen or carbon dioxide. If sources of ignition are excluded and/or a large excess of gas which does not form flammable mixtures with the volatile substances is used, other gases, preferably air, may also be employed.

Cesium and/or rubidium can be applied to the washed (dried and undried) catalyst in various ways, it is only important that the indicated amounts of cesium, rubidium or mixtures thereof are applied to the total amount of used catalyst, possibly including partial amounts that have not been washed).

The cesium and/or rubidium are applied to the catalyst suitably by wetting (soaking, impregnating) with an impregnating liquid containing one or several compounds of cesium and/or rubidium.

The impregnating liquid should contain the cesium and/or rubidium compounds in a form which is as finely divided as possible. The compounds may be present in dispersion or emulsion, buty they are preferably used in dissolved form (impregnating solution).

As solvent or liquid phase of a dispersion or emulsion the inorganic and organic liquids described above and used as washing liquid can be ued. Preferred solvents are aliphatic, alicyclic or aromatic hydrocarbons, preferably those having from 5 to 10 carbon atoms such as pentane, hexane, heptane, cyclohexane, benzene; aliphatic, alicyclic or aromatic ethers, preferably aliphatic or alicyclic ethers having from 3 to 10 carbon atoms, for example diethyl ether, methylethyl ether, dipropyl ether, methylisopropyl ether, tetrahydrofurane, dioxane; aliphatic, alicyclic or aromatic ketones, preferably aliphatic ketones having from 3 to 10 carbon atoms, for example acetone, methylethyl ketone, ethylpropyl ketone; aliphatic or aromatic esters, preferably aliphatic esters having from 3 to 10 carbon atoms, for example methyl acetate, ethyl acetate; and aliphatic, alicyclic or aromatic alcohols, preferably aliphatic or alicyclic alcohols having from 1 to 6 carbon atoms.

Especially preferred are aliphatic (linear or branched) alcohols having from 1 to 6 carbon atoms, more preferably 1 to 3 carbon atoms such as methanol, ethanol, propanol, isopropanol.

The organic solvents can be used either individually or in admixture with one another or in admixture with water. Pure water can also be used as solvent. If mixtures of organic solvents and water are used, those are preferred which contain up to 40% by weight, preferably up to 20% by weight, of water, calculated on the total liquid.

The type of the cesium and/or rubidium compounds is not important to the effect according to the invention. In general, the compound(s) used contain cesium and rubidium in the form of the cations. It is of little importance with which radical (anion) the cesium and/or rubidium is associated. These radicals may be inorganic or organic but they should not consist of substances which, especially after the treatment with the gaseous reaction mixture for the production of ethylene oxide act as a so-called catalyst poison. Suitable inorganic compounds are preferably inorganic salts, for example sulfates, nitrites, nitrates, chlorides, bromides, iodides, fluorides, chlorates, silicates, carbonates, bicarbonates and cyanates; as well as hydroxides and oxides; suitable organic compounds are preferably organic salts such as formates, acetates, oxalates, malonates, succinates, butyrates, laurates, stearates, lactates, tartrates and benzoates, as well as alcoholates, for example methylate, ethylate and phenolate. There are preferred inorganic and organic salts, especially the formates, acetates, carbonates, bicarbonates, nitrates, hydroxides and alcoholates of aliphatic alcohols having from 1 to 6 and preferably from 1 to 3 carbon atoms.

One or more cesium or one or more rubidium compounds may be used and mixtures of one or more cesium compounds and one or more rubidium compounds are also suitable.

The concentration of the cesium and/or rubidium compound(s) in the impregnating liquid is not critical. In general, it depends on the solubility of the compounds. It is only important that after the treatment of the catalyst with the impregnating liquid the content of cesium and/or rubidium on the catalyst is in the range of from 1 to 1,000 mg/kg (the concentration of cesium or rubidium on the catalyst only refers to the respective metal, the other part not being considered).

The impregnating liquid should have a minimum concentration of 0.0003% by weight of cesium and/or rubidium. It proved advantageous to use a solution having a concentration of cesium and/or rubidium compound of 0.005 to 1.0% by weight, preferably 0.01 to 0.4% by weight, relative to the impregnating liquid. The concentration of the impregnating liquid depends in all cases on the desired concentration of rubidium or cesium on the catalyst.

The amount of impregnating liquid can be varied within wide limits. It depends on the amount of catalyst to be treated and should be so large that all catalyst particles are completely wetted. Hence, there is no upper limit as to the amount of impregnating liquid with regard to the effect. In general, 75 to 150% by volume of impregnating liquid will be used, relative to the catalyst to be treated.

The washed catalyst can be treated with the impregnating liquid in order to apply from 1 to 1,000 mg/kg, preferably from 3 to 500 mg/kg, of cesium and/or rubidium according to various methods. A suitable mode of operation is the soaking (wetting, impregnating) as described in German Patent specification 2,519,599 according to which the impregnating liquid is poured over the catalyst and the excess portion is drained. The impregnating may be carried out in a container, optionally with stirring or in one or several tubes wherein the catalyst is arranged as a fixed bed. The latter method is especially suitable in industrial scale installations in which the catalyst is contained in the tubes of the reactor. The impregnating liquid can be poured over the catalyst once or several times; either the separated liquid or a freshly prepared impregnating liquid being used.

According to another mode of operation a concentration gradient of from 0.5 to 20 mg/kg per meter, preferably 1 to 15 mg/kg per meter, of cesium and/or rubidium is produced over at least 2 and preferably 5 to 20 meters of fixed bed, opposite to the direction of flow of the gases to be reacted. In this case, the average content of cesium and/or rubidium of the supported silver catalyst after the treatment is expediently 10 to 1,000 mg/kg. Individual sections of the solid bed of catalyst particles may have concentrations of cesium and/or rubidium lower than 10 and higher than 1,000 mg/kg. On the other hand, the catalyst sections should contain at least 1 mg/kg of cesium and/or rubidium, since below this concentration the catalyst does no longer have the advantageous effet and the particles unnecessarily occupy space in the solid bed.

The solid bed of catalyst treated with the impregnating liquid and passed by the gases to be treated should have a length of at least 2 meters. An upper limit of the length of the catalyst layer passed by the gases is only given by industrial and economical considerations, it may be 40 meter and more, a length of 5 to 20 meters being preferred.

To produce the aforementioned concentration gradient on the washed catalyst the following process proved to give good results: Separate portions of the washed silver catalyst are wetted with impregnation solutions having different concentrations within the range of 0.003 to 0.6% by weight, relative to the solution, of cesium and/or rubidium in the form of the chosen compound(s) and each catalyst portion remains in contact with the impregnating solution for about 3 to 120 minutes. The catalyst portions are then arranged in the reactor in such a manner than the cesium and/or rubidium concentration of the impregnating solutions used for the catalyst treatment continually inceases in the direction of flow of the gases to be reacted. The increase of the cesium and/or rubidium concentration in the impregnation solutions used can be non uniform but preferably it is uniform. Good results are obtained with an increase in concentration of 3 to 30% over the lowest concentration or the respective preceding concentration. The number of catalyst portions is limited by industrial and economical considerations only. In principle, there may be used any number of catalyst portions but preferably 3 to 20 portions are treated with an equal number of impregnating solutions of different concentrations. Comparing the technical expenditure and effect, especially good results are obtained with 5 to 15 catalyst portions which may be different in size from one another but preferably they are equal.

The catalyst portions can be wetted with the impregnating solutions, for example, by spraying or pouring over. It proved especially simple and effective to put the respective catalyst portion in a container and to pour the impregnating solution over the catalyst up to a level a little above the level of the catalyst particles. After a time of action of about 3 to 120 minutes, the excess impregnating solution is separated.

The application of 1 to 1,000 ppm, preferably 3 to 500 ppm, of cesium and/or rubidium to the washed catalyst can also be performed in two or more steps, preferably two to five steps, that means the catalyst is applied in portions. In this case the catalyst is used again for the direct oxidation of ethylene to ethylene oxide with molecular oxygen or air after each application step. The periods of time during which the catalyst is in use after each individual application can vary within wide limits, generally it is between 1 week and several months, preferably between 1 and 20 weeks and more preferably 3 to 5 weeks. The period of time is limited by industrial-economical considerations; the lower limits should not be below 1 hour.

The amount of cesium and/or rubidium applied onto the washed catalyst in each step can be varied between 1 and 1,000 mg/kg, preferably 3 to 500 mg/kg. In general, at least 1 mg/kg and preferably from 3 to 100 mg/kg will be applied in the first step and in each following step the same amount or a fraction thereof will be applied.

After the treatment of the washed catalyst with impregnating liquid by a method as described above, the remainders of liquid still adhering to the catalyst, if any, after the separation of the major portion of the impregnating liquid, should be removed, which can be done by one of the aforedescribed drying processes. The temperatures to be used depend, in this case too, on the impregnating liquid to be evaporated and are in the range of from 50° to 250° C., preferably 50° to 150° C., more preferably 70° to 120° C.

The process of the invention is independent of the type of the silver catalyst, for example as regards composition and structure. Any catalyst suitable for the direct oxidation of ethylene to ethylene oxide with molecular oxygen or air can be subjected to the process of the invention.

Silver catalysts for the direct oxidation of ethylene to ethylene oxide with molecular oxygen or air as well as the direct oxidation itself are described in detail in literature, for example in U.S. Pat. Nos. 2,615,899; 3,899,445 and 3,962,136.

In general, the silver catalysts used consist of 1 to 40% by weight (calculated on the total catalyst) of silver on a carrier material and optionally of smaller or larger amounts of the most different promoters or co-activators. The silver is deposited as metal on the inner and outer surfaces of the carrier material, which is preferably porous, and distributed on the surface as uniform as possible. The morphologie of the silver deposited on the carrier material can vary within wide limits. In general, it has the shape of spherical particles having a diameter of 0.01 to 10 microns. The carrier preferably consists of of a porous and heat resistant material that remains inert under the conditions of the direct oxidation of ethylene.

Materials of this type are, for example, aluminium compounds, preferably aluminium oxides of different structures, magnesium oxides, kieselguhr, pumice, silicium dioxide, silicum carbide, clay, corundum, zeolithes, metal oxides and the like. Aluminum oxides are especially preferred carrier materials because of their substantially uniform pore diameter. They are characterized by the specific surface ($m^2/g$), the specific pore volume (cc/g) and the average pore diameter (micron). In general, the carrier material is used in the form of granules, balls, pieces, rings, or the like.

The two-stage process according to the invention is suitable for used silver catalysts, the term used being intended to indicate that the catalyst has already been in use in the reaction of ethylene to ethylene oxide with molecular oxygen or air. It is immaterial whether its original selectivity has subsided or not. The time during which the catalyst to be treated was in use for the oxidation of ethylene to ethylene oxide prior to the treatment according to the invention can vary between a few weeks (1 to 3) and several years (1 to 10) and more. It is not absolutely necessary that the activity of the catalyst has subsided, i.e. its selectivity is reduced, (which is generally the case after a prolonged time of use), it may also have retained its original selectivity.

By the combination according to the invention of a washing procedure with the application of cesium and/or rubidium the activity of supported silver catalysts, which have been in use for the direct oxidation of ethylene with molecular oxygen or air, can be improved considerably. The activity of a catalyst can be expressed as the conversion of ethylene (in %) at a given temperature or as the molar proportion of ethylene transformed into ethylene oxide, its selectivity. A catalyst is the more effective the higher the amount of ethylene reacted at a given temperature, the higher the selectivity with a given conversion and the lower the temperature to obtain a given conversion.

The process of the invention makes it possible to increase considerably not only the selectivity of used supported silver catalysts, but also the rate of conversion. Moreover, with the use of the catalysts treated according to the invention the reaction temperature can be lowered—with the same or even increased conversion. This fact is especially important since, at a lower reaction temperature, the formation of undesired by-products, such as carbon dioxide, formaldehyde, acetaldehyde, is strongly reduced. With regard to the important amounts of ethylene oxide produced by the ethylene oxidation process, an increase in yield, be it only a few percent or even a few tenths of a percent, is of considerable economical importance. The process of the invention has the further advantage that it can be carried out in the usual large-scale production plants (with commercial supported silver catalysts) without noticeable additional expenditure of energy, investment and material.

The following Examples illustrate the invention.

The examples and comparative examples were carried out in a test reactor consisting of a vertical chrome-vanadium steel reaction tube having an internal diameter of 30 mm and a length of 300 mm. The reaction tube provided with a jacket was heated with hot oil flowing through the jacket. Up to a height of 200 mm, the reaction tube was filled with $\alpha$-$Al_2O_3$ pellets serving to pre-heat the feed gas. On top of the inert charge, the catalyst to be tested was placed. The feed gas was introduced (without pressure) at the bottom and left the reaction tube at the head.

The gas mixture used consisted of:

28% by volume of $C_2H_4$
53% by volume of $CH_4$
8% by volume of $O_2$    gas mixture I
5% by volume of $CO_2$
6% by volume of $N_2$
0.0002% by volume of vinyl chloride (as inhibitor)
or of
4% by volume of $C_2H_4$
5% by volume of $O_2$
4% by volume of $CO_2$    gas mixture II
87% by volume of $N_2$
The space-time-velocity amounted to
$$250 \cdot \frac{\text{parts by volume of gas}}{\text{hour} \cdot \text{parts by volume of catalyst}}$$

The gas issuing at the reactor outlet was analyzed by gas chromatography and conversion and selectivity were calculated. The temperature of the heat carrying medium was varied until a constant ethylene conversion of 7% in gas mixture I and of 35% in gas mixture II was obtained. The reactions were continued until the measured values did no longer change, which was normally the case after 200 hours.

In the tests commercial supported silver catalysts were used which consisted of 10% of silver (particle diameter 1 to 5 microns) on $\alpha$-$Al_2O_3$ as carrier material in the shape of rings having a height of 8 mm, an outer diameter of 8 mm and an inner diameter of 2 mm in the case of catalyst I, or in the shape of cylinders having a diameter and a height of about 5 mm in the case of catalyst II, the specific surface being from 0.1 to 0.5 $m^2/g$.

The content of cesium and/or rubidium applied to the catalyst was determined by atom absorption spectroscopy (cf. "Absorptionsspectroscopie" Bernhard Wells, Verlag Chemie 1972, pages 114 et seq.). The analysis was carried out in an air/acetylene flame and the atom absorption in the emission was measured.

EXAMPLE 1

In a 100 ml Erlenmeyer flask 50 ml of methanol were poured at 25° C. over 50 g of commercial catalyst II, which had been used for 10 hours for the manufacture of ethylene oxide by direct oxidation of ethylene with oxygen, and the mixture was left to stand for 5 hours. The methanol was decanted and another 50 ml of methanol were poured over the catalyst. After 5 hours, the methanol was again poured off. After the methanol wash, a solution of 50 ml of methanol and 0.0205 g of cesium nitrate was poured over the catalyst moist with methanol in the 100 ml Erlenmeyer flask. The mixture was left to stand for 1 hour, the impregnating solution was poured off and the catalyst was dried for 1 hour at 110° C. in a drying cabinet. The catalyst had then a cesium concentration of 90 mg/kg.

The catalyst treated in this manner was introduced into the test reactor and gas mixture I was passed through. The selectivity rose form initially 69% to 76%.

COMPARATIVE EXAMPLE 1

The test was carried out as described in Example 1 with the exception that the catalyst was not washed with methanol. In this case, the selectivity rose from 69% to 74.5%.

EXAMPLE 2

In a 100 ml Erlenmeyer flask a washing liquid of isopropanol and 20% by weight of water, calculated on the total liquid, was poured, in three repetitions, over 50 g of the catalyst II. After the last decantation, the washed catalyst was treated as described in Example 1 with a solution of 0.020 g of cesium carbonate in 50 ml of methanol and then tested. The cesium concentration on the catalyst was found to be 91 mg/kg. The selectivity rose from initially 69% to 76%.

COMPARATIVE EXAMPLE 2

The test was carried out as described in Example 2 with the exception that the catalyst was not washed. The selectivity rose from 69% to 74%.

EXAMPLE 3

A glass tube having an internal diameter of 20 mm and a length of 500 mm was charged with 100 g of catalyst I which had been used for 5 months in a pilot plant for the manufacture of ethylene oxide from ethylene and oxygen. At room temperature 500 g of benzene containing 10% by weight of dioxane, relative to the total mixture, were pumped through the catalyst during the course of 1 hour (in upward direction). After draining of the washing liquid, a solution of 0.042 g of cesium acetate in 100 ml of methanol was poured over the catalyst in the glass tube and the whole was left to stand for 1 hour. The impregnating solution was then allowed to run off and the silver catalyst was dried for 1 hour at 110° C. in a drying cabinet. The cesium concentration of the catalyst was 88 mg/kg.

The catalyst treated in this manner was filled into the test reactor and tested with gas mixture I under the specified conditions.

The selectivity rose from initially 68% to 74%.

COMPARATIVE EXAMPLE 3

The test was carried out as described in Example 3, with the exception that the catalyst was not washed. The selectivity rose from 68% to 72.5%.

EXAMPLE 4

In a 200 ml Erlenmeyer flask 100 g of acetone were poured at 25° C. over 100 g of commercial silver catalyst I, which had been used for the manufacture of ethylene oxide from ethylene and oxygen for 4 years and the whole was left to stand for 1 hour. After decantation of the washing liquid, another 100 g of acetone were poured over the catalyst and decanted after 1 hour.

After the acetone wash, the catalyst was divided into 5 equal portions. One portion was soaked in a 50 ml Erlenmeyer flask in 30 ml of an ethanolic solution containing 285 mg of cesium sulfate per kg of ethanol and left to stand for 1 hour. After decantation of the excess amount of impregnating solution, the catalyst portion was dried for 1 hour at 110° C. in a drying cabinet. The other 4 portions were impregnated in the same manner with solutions containing 333, 381, 428 and 476 mg, respectively, of cesium sulfate per kilogram of ethanol and dried.

The treated catalyst portions were filled into the test reactor in such an order that the portion having the lowest cesium content came first into contact with gas mixture I and the other portions were arranged according to their increasing cesium content. The selectivity rose from 66 to 75%.

COMPARATIVE EXAMPLE 4

The test was carried out as described in Example 4, with the exception that the catalyst was not washed with acetone.

The selectivity rose from 66% to 73.5% only.

EXAMPLE 5

100 g of commercial silver catalyst I, which had been used for 12 months in a pilot plant for the manufacture of ethylene oxide from air and ethylene, was introduced into a glass tube having an internal diameter of 20 mm and a length of 500 mm. By means of a pump, 400 ml of petroleum ether boiling at 40° to 70° C. were pumped at 25° C. in upward direction through the catalyst. After leaving the bed, the first 100 ml of petroleum ether were rejected and the remaining 300 ml were recycled for 1 hour at a rate of 0.5 l per hour.

Next, the petroleum ether was allowed to flow off and the catalyst was dried for 1 hour with 100 l of nitrogen per hour while being heated to 60° C. by means of a heat carrying medium circulating in the jacket of the glass tube. After cooling to 25° C., a solution containing 500 mg of cesium nitrate per kg of methanol was poured over the catalyst in the glass tube. After 1 hour, the impregnating solution was drained and the catalyst was dried by passing over 100 l of nitrogen for 1 hour at 80° C.

The catalyst was then introduced into the test reactor and tested in the described manner with gas mixture II. The selectivity rose from 60 to 67%.

COMPARATIVE EXAMPLE 5

The test was carried out as described in Example 5, with the exception that the catalyst was not washed with petroleum ether.

The selectivity rose from 60 to 65%.

What is claimed is:

1. Process to improve the activity of supported silver catalysts which have been used for the direct oxidation of ethylene to ethylene oxide with molecular oxygen or air by applying to the catalyst from 1 to 1,000 parts, per 1 million part of catalyst, of cesium, rubidium or a mixture thereof, which comprises washing the catalyst with an inert organic liquid prior to the application of cesium rubidium or mixture thereof.

2. A process as claimed in claim 1, wherein the washing liquid is an organic liquid boiling at a temperature of from 15° to 250° C.

3. The process of claim 2, wherein the washing liquid boils at 20° to 150° C.

4. A process as claimed in claim 1, wherein the washing liquid used is selected from the group consisting of
   aliphatic, alicyclic and aromatic hydrocarbons having from 5 to 10 carbon atoms,
   aliphatic and alicyclic ethers having from 3 to 10 carbon atoms, aliphatic ketones having from 3 to 10 carbon atoms,
   aliphatic esters having from 3 to 10 carbon atoms and
   aliphatic or alicyclic alcohols from 1 to 6 carbon atoms and mixtures thereof.

5. The process of claim 4, wherein the washing liquid is an aliphatic hydrocarbon having from 5 to 10 carbon atoms, petroleum ether, cyclohexane, benzene, an aliphatic ether having from 4 to 8 carbon atoms, dioxane, tetrahydrofurane, an aliphatic ketone having from 3 to 6 carbon atoms, an aliphatic alcohol having from 1 to 3 carbon atoms, or a mixture thereof.

6. A process as claimed in claim 1, wherein the catalyst is washed in a container by pouring the washing liquid thereover 1 to 5 times, the mixture of washing liquid and catalyst is left to stand for 1 to 5 hours and the washing liquid is then decanted.

7. A process as claimed in claim 1, wherein the catalyst is washed by flooding.

8. A process as claimed in claim 1, wherein the catalyst is washed at a temperature of from 10° to 100° C.

9. A process as claimed in claim 1, wherein 3 to 500 ppm of cesium, rubidium or mixture thereof are applied to the catalyst after washing.

10. A process as claimed in claim 1, wherein the catalyst is impregnated with a solution containing from 0.005 to 1.0% by weight of a cesium, rubidium or mixture thereof compound(s) and the portion of the solvent remaining on the catalyst is removed by heating.

11. A process as claimed in claim 1, wherein 3 to 20 catalyst portions are impregnated with the same number of impregnating solutions having different cesium and/or rubidium concentrations in the range of from 0.003 to 0.6% by weight, the solvent remaining on the catalyst portions is removed by heating and the catalyst portions are used for the direct oxidation in such an order of succession that the cesium rubidium or mixture thereof concentration in the impregnating solutions with which the catalyst portions have been treated increase in the direction of flow of ethylene and oxygen or air.

12. A process as claimed in any one of claims 10 and 11, wherein an inorganic or organic salt, hydroxide or alcoholate of an aliphatic alcohol is used as the cesium, rubidium or mixture thereof compound(s) and one or several aliphatic alcohols having from 1 to 6 carbon atoms, or said aliphatic alcohols in admixture with up to 40 percent by weight of water, calculated on the impregnating solution, are used as solvent for said cesium, rebidium or mixture thereof compound(s).

* * * * *